(12) United States Patent
Shukla

(10) Patent No.: US 11,224,556 B2
(45) Date of Patent: Jan. 18, 2022

(54) INHALER COMPLIANCE DEVICE AND MONITORING SYSTEM

(71) Applicants: Manan Shukla, Roslyn Heights, NY (US); Mayank Shukla, Roslyn Heights, NY (US)

(72) Inventor: Manan Shukla, Roslyn Heights, NY (US)

( * ) Notice: Subject to any disclaimer, the term of this patent is extended or adjusted under 35 U.S.C. 154(b) by 0 days.

(21) Appl. No.: 17/016,111

(22) Filed: Sep. 9, 2020

(65) Prior Publication Data
US 2020/0405579 A1 Dec. 31, 2020

Related U.S. Application Data

(63) Continuation-in-part of application No. 16/746,801, filed on Jan. 17, 2020, now Pat. No. 10,881,585, which is a continuation of application No. 16/218,426, filed on Dec. 12, 2018, now Pat. No. 10,588,825, which is a continuation-in-part of application No. 15/952,972, filed on Apr. 13, 2018, now abandoned.

(60) Provisional application No. 62/485,730, filed on Apr. 14, 2017.

(51) Int. Cl.
*G08B 1/08* (2006.01)
*A61J 7/04* (2006.01)
*G16H 20/13* (2018.01)
*A61J 1/03* (2006.01)

(52) U.S. Cl.
CPC .............. *A61J 7/0436* (2015.05); *A61J 1/03* (2013.01); *G16H 20/13* (2018.01); *A61J 2200/30* (2013.01)

(58) Field of Classification Search
CPC .............................. A61J 7/0436; G16H 20/13
USPC ............ 340/539.1, 517, 521, 532, 540–541; 128/200.14, 200.23, 203.12
See application file for complete search history.

(56) References Cited

U.S. PATENT DOCUMENTS

| 6,422,234 B1 * | 7/2002 | Bacon ............... A61M 15/0091 128/200.14 |
| 7,331,340 B2 * | 2/2008 | Barney ............. A61M 15/0065 128/200.23 |
| 2014/0007867 A1 * | 1/2014 | Bruin .................. A61M 15/009 128/200.23 |

(Continued)

*Primary Examiner* — Tai T Nguyen
(74) *Attorney, Agent, or Firm* — Alfred M. Walker; John F. Vodopia

(57) ABSTRACT

An aerosol mist compliance device maintains a patient's aerosol supply and monitors the patient's access to pills contained in the device to memorialize the patient's compliance with his/her respiratory inhalation regimen. The device has a housing, including an inner aerosol mist storage compartment and an electronics unit, a removable mouthpiece cap, a switch to detect removal of the mouthpiece cap and magnet away from the housing, and to detect a replacement of the mouthpiece cap and magnet to the housing, wherein activating the switch triggers a transition from an active state, to a dormant state, and vice versa. A transition from the dormant state to the active state, by replacing the mouthpiece cap to the housing generates an aerosol-taken signal. A microcontroller generates a compliance notification signal that is communicated to a Wi-Fi module or router within or attached to the electronics unit, to memorialize the apparent compliance.

17 Claims, 4 Drawing Sheets

(56) References Cited

U.S. PATENT DOCUMENTS

2016/0325057 A1\* 11/2016 Morrison .......... A61M 15/0065

\* cited by examiner

INHALER COMPLIANCE DEVICE AND MONITORING SYSTEM

RELATED APPLICATIONS

This application claims priority in part under 35 U.S.C. § 120 from U.S. patent application Ser. No. 16/746,801, filed Jan. 17, 2020, now U.S. Pat. No. 10,881,585 dated Jan. 5, 2021. The '801 application is a continuation of application Ser. No. 16/218,426, filed Dec. 12, 2018, now U.S. Pat. No. 10,588,825 dated Mar. 17, 2020. The '426 application is a continuation-in-part of U.S. patent application Ser. No. 15/952,972 filed on Apr. 13, 2018. The '972, 426, and '801 applications are incorporated by reference herein. The '972 application also claims benefit under 35 USC § 119 (e) from provisional application No. 62/485,730 filed Apr. 14, 2017. The '730 application is incorporated by reference herein.

INCORPORATION BY REFERENCE

This application incorporates the subject matter of Applicant's U.S. Pat. No. 10,588,825 B1, issued Mar. 17, 2020, which '825 patent was filed as U.S. patent application Ser. No. 16/218,426, filed Dec. 12, 2018.

FIELD OF THE INVENTION

The present invention relates to dispensing and monitoring adherence to the correct inhalation of prescribed pharmaceutical metered aerosol dosages for a medical patient.

BACKGROUND OF THE INVENTION

As noted in Applicant's U.S. Pat. No. 10,588,825 B1, the present invention relates to dispensing and monitoring adherence to the correct inhalation of prescribed pharmaceutical metered aerosol dosages for a medical patient.

There are many reasons and consequences behind medical noncompliance. Reasons behind compliance can include correlations between race, gender, age, in addition to avoidable hospitalization, false results in clinical studies, and decreased efficiency for doctors, pharmacists and other medical personnel.

Although there have been some solutions to such a problem, little is done overall to solve it. Even the most effective technologies in the market, pill bottles, are either too expensive, or do not solve the initial problem of noncompliance. There is a need to be able to provide immediate compliance efficiently and effectively to the patient, doctor, pharmacist, and other healthcare providers. In addition, there is a need to provide a reminder system to limit unintentional compliance such as forgetfulness. This is incredibly beneficial to doctors because not only is noncompliance limited, pill compliance device of Applicant's '825 patented pill compliance device, the Medicobox™ can help doctors decide on the next course of action, such as prescribing another drug.

As noted in 2014, the United States healthcare rose to three trillion dollars, with a projected increase of 5.8% by 2025. The cost per capita of the healthcare system has risen by approximately 3,000 dollars since 2004, and is expected to rise by 4.8% over the coming years. Contrary to intuition, however, the healthcare of the United States strays behind other first-world countries such as Australia, France, Canada, etc. although it spends the most out of these countries.

These rankings are due to a significant amount of waste, which arises from multiple sources, the first of which is the failure of proper care delivery, in which execution of proper care processes, or methods are not able to be delivered properly to the patient. By implementing solutions towards this problem can alone potentially save approximately 100 billion dollars. Secondly is overtreatment, in which unnecessary and excessive amounts of medication and/or other treatments are administered to the patient. This not only wastes money, but also does not enhance or improve the patient's health regimen. This portion can potentially save approximately 158 billion dollars. Finally, fraud and abuse, which involves scams, and corrupt medical practices. Solving such problems would save approximately 82 billion dollars. In total, approximately 750 billion dollars are wasted by the United States, which could be used more effectively in other fields of the government. Table 2 represents this healthcare expenditures divided into its respective causes.

As noted in Applicant's '825 patent, to create an effective analogy to provide a realization of this cost, the United States spent 757 billion dollars within the span of eight years in the Iraq war. In contrast, 750 billion dollars are simply wasted every year by the health system.

In addition, investment is not contributed to either research or development, resulting in the significant waste today. To take the example of GOOGLE®, one can first analyze the holistic revenue of the company itself—approximately 74.54 billion dollars per year. Out of this, approximately 8 billion is spent on research and development. The research and development portion of the 3 trillion healthcare budget is simply 1 billion dollars, too meager for any major problem to be resolved.

However, the most wasteful but overviewed practice today is noncompliance. Occupying a third of healthcare waste of resources, noncompliance is the origin and root of healthcare waste in the United States.

Defined as the degree of impassiveness of a patient in adhering to advice given by a prescriber or doctor, medical noncompliance has surpassed all other crises faced in healthcare today. Medical noncompliance is a very broad issue; therefore, the term medication noncompliance, which is specifically the act of not taking medication as advised by the healthcare provider or simply not taking medication at all is used. Note that both terms medical noncompliance and medication noncompliance will be used interchangeably for the sake of a lack of confusion.

Approximately 25-50% of Americans were noncompliant with their medication as of 2012, and this value increased as the population of adults having at least one prescription increased from 38% between 1988-1994 to 49% between 2007-2010—due to the fact that more adults are administering medication. Because the number of patients with chronic diseases have also increased on average by at least 77% in older adults, one can predict a rise of noncompliance in the near future of healthcare—which would also create an expense of over at least 10 billion dollars. Over the rest of this paper, problems and solutions to the problem of medical noncompliance will be discussed, and how implementation of different solutions such as the Medicobox™ pill compliance device will increase the efficiency and cost-effectiveness of healthcare.

There is a major difference when one considers the terms compliance and adherence in terms of medical definitions. In the rest of this essay, although the terms adherence and compliance will be used interchangeably, clear distinction in connotations must be established. "Compliance", unlike "adherence", tends not to be as prevalent in the health industry as much as the word "adherence" does because "compliance" implies an obligation of the patient towards the doctor's advice over the true reality, in which a therapeutic alliance is formed between the doctor and patient, as demonstrated by the term adherence. These terms, however distinctive, will be used interchangeably throughout the paper.

To solve the immense problem of non-adherence, one must look into the current methods of adherence measurement. Adherence is measured as the percentage of the amount of medication the patient has taken over a select period of time. This generality can be specified by including the time and dosage of the administration of medication based on the prescription of the patient specifically. Other methods of measuring adherence are by determining the medication possession ratio (MPR), or determining the proportion of days covered (PDC). MPR is measured by the amount days a certain refill is supposed to persist, over the amount of days the medication is in the possession of the patient (such as the time between the first day and the day the patient comes for a refill).

This is shown below in Table 4.

The second method, PDC, is calculated by the amount of days supplied by the pharmacist over the number of days in the interval (Table 5). When both calculations lead to a percentage higher than 80%, the patient is said to be adherent or compliant.

However, both methods have subtle differences between one another. For example, for patients with 3 regimens to be administered in a day, but administers only one regimen per day would be accounted for in MPR calculations; however, under PDC calculations, the specific patient will not be accounted for until all three pills are taken by the patient. Therefore, PDC is a more accurate measure to track compliance. Both methods, along with questionnaires are used by clinics and doctors to determine adherence for indirect purposes. To measure adherence directly, direct observation of patient is done. In addition, testing of urine or other bodily fluids can be done to determine whether certain medication has been taken. However, this is rarely used as it is very costly, and inefficient for medical personnel.

Already one can view flaws in the method used to measure adherence in healthcare. However indirect measures taken by doctors and nurses are used in the twenty-first century, not only are they accurate, it is not a viable resource for the healthcare industry to use as there are multiple leeways that can be utilized by patients to provide incorrect, falsified, or misleading evidence of adherence. For example, a patient may simply bring back an empty container claiming that he/she has taken the medication; meanwhile, the remaining pills are compiled into another container, to which the pharmacist does not have the knowledge of.

This situation can simply be represented in the following case study: A 53-year-old man was diagnosed with insulin resistance and type 2 diabetes mellitus. To treat this, the doctor advised him to "modify his diet, increase his level of activity as much as possible, and finally was prescribed oral metformin to be taken with meals". However, after a three-month follow-up, the patient's status does not change: his weight is the same, hemoglobin levels do not decrease significantly. The patient admits to not having enough exercise, nor did he try to change his eating habits. However, he asserted that he has been taking his medication as directed. Before prescribing another medication for the patient, the doctor first decides to check whether the patient is actually adhering to the prescription. He instructs the patient to bring in his pill bottle in the next follow-up. Next, the doctor calls the local pharmacy, and finds that the patient did come for a refill in a timely manner. In the next follow up, the patient confessed that he did not take his pills as prescribed by the doctor, his reason being that he was "too tired", or "forgot to take his medication." In addition, the patient stated that he has more pills at the medicine cabinet at his house. When using the methods of measuring compliance such as the MPR or PDC method, one can see that the current adherence measurement methods do not apply or are not helpful in this case study. Healthcare personnel such as physicians can potentially be misled when encountering such a scenario.

The problem of non-adherence has led to drastic consequences affecting the patient, the doctor, employer, pharmacist, etc. One consequence of noncompliance is the number of avoidable, unnecessary hospitalizations. A vast contribution to the cost of avoidable healthcare wastes, 213 billion dollars are wasted due to avoidable hospitalization. Avoidable hospitalization due to noncompliance not only decreases the number of patients who can be cured in a certain period of time, but it also causes unnecessary financial pressures on patients, employers and employees. Because of continual visits to the hospital and the average income being approximately 50,000 dollars in 2014, patients can no longer afford the high cost of hospitalizations. This is due to the fact that without insurance, three-day hospitalizations cost approximately 30,000 dollars—more than half of the average income of the average person in the United States. This is not including the cost of medication itself. Hepatitis C pills cost 1000 dollars per pill without insurance—meaning that a four month-period of medication can cost approximately 84,000 dollars—too high for patients to pay for them. Since more patients cannot enter the hospital for care, hospital employers can no longer receive the profits and income that they had before—as antidote, healthcare prices are increased to restore profits for the hospital. As shown in Table 6, approximately 8 million dollars can be saved by hospitals if adherence is increased, not including the great number of potential lives increased adherence can save.

Associations have also been made with increased noncompliance and hospitalization, and mortality rates. In a study of 557 patients suffering from cardiovascular disease, non-adherence was associated with doubling of mortality rates and increased hospitalizations. In addition, studies have shown that higher rates of noncompliance of the patient lead to a higher risk of developing a serious disease or side-effect. Studies have also shown noncompliant patients with diseases such hypoglycemia develop and acquire other complications such as acute myocardial infarction once noncompliance has reached a certain degree. Similar results have been displayed in diabetes, in which higher rate of noncompliance can potentially lead to increased levels of glycosylated hemoglobin, blood pressure, and cholesterol levels. This leads to a higher rate of hospitalization of the patient. Statistics show that one-third of all hospitalizations involving adverse reactions are due to non-adherence. 69% of all of the money wasted in healthcare is due to this problem. Finally, non-adherent patients are 17 percent more likely to be hospitalized than adherent patients and are subjected to a higher medical bill (by approximately 3757 dollars) than one who is adherent. These devastating statistics show us the immediate need to lower non-adherence. On the other hand, increased compliance, as shown in Table 7 shows a study in which increased adherence have been linked to decreased hospitalization.

Another consequence of non-adherence is the effect that noncompliance has on clinical outcomes. Non-adherence that occurs during clinical trials are known as artifactual non-adherence. In these trials, adherence is assumed under ideal conditions—in which all medication is taken as prescribed. Such is the case of the Ideal Trial, which is a double-blind experiment where adherence is perfect:

A sample of participants are split into two groups: Group A which will receive the placebo, and Group B, which will receive the experimental drug. Neither the doctor nor the participant knows which drug is administered or received. All participants take their pills as assigned and report for refills at the correct time. Data is recorded at the proper time, and a conclusion regarding the difference between the two treatments.

One can definitely infer that in reality, this does not ever happen. Statistics displays that this is most definitely false—both real world situations and experimental (simulated) situations, non-adherence thrives among the population. Non-adherence is not limited to taking medication in regards of the prescription—in clinical trials, participating in multiple trials at once is also considered artifactual due to the fact that certain drugs can conflict outcomes. This leads to misleading evidence, which interferes accurate hypothesis testing and conclusions, with results that may be detrimental to the population. Average adherence rate in trials is only 34-78%. This is in addition to the 30% who dump their medications before study visits. At the same time, deceptive and artifactual evidence can be completely unrelated to the hypothesis being tested—which leads to a waste of money, and a waste of time, as shown in Table 8.

In the following case study, low, or no adherence can cause problems in clinical trials:

A 42-year-old male participating in a schizophrenia study was also participating in another study. While explicitly stating that he is not currently participating in another study, he laughed when confronted about the issue, stating "you caught me". In addition, he admitted to only take the medication when his "head felt clearer", although he had previously reported a 100% adherence by pill count.

Such a problem can occur with other individuals, which leads to a higher inaccuracy in data selection. Multiple or coupled non-adherence can lead to a higher impact on study power. For example, if approximately 30% of patients are noncompliant and do not give reliable data, then the study's results would be powered to approximately to 85% to 95%, where a true power would result to be 60% to 70%. This is further exemplified in Table 9.

Powering the data of an experiment using noncompliance is definitely detrimental. This is represented in the following case study:

In 2004, the New England Journal of Medicine published the results of a study of the Women's Health Initiative regarding Calcium and Vitamin D in relation to Osteoporosis. The trial was established to provide a supplement given over the counter to reduce the amount of fractures resulting in postmenopausal women. Such a trial involved approximately thirty thousand women, and seven years' worth of data.

Although such an experiment was deemed an achievement, results did not conclude as expected. Conclusions were made, but with multiple sources of error. By the end of the trial, an enormous number of women did not take their pills. Approximately 24% admitted to not take medication, while only 59% were taking 80% of the medication as prescribed. This was measured by a pill recount method, which actually overestimates compliance.

This creates the hypothetical question which dictates whether such trials involving so much noncompliance should be acknowledged as reliable. With an incredible amount of money put on such a project, pressures on scientists, and experimenters can be forced to make conclusions, even though such conclusions can easily be rejected. In addition, trials that may be on the path to producing drugs that may have the potential to eradicate the world of potent diseases may be biased, falsified, or simply inaccurate of the population—leading to potential damage to the entire population, or creating extraneous complications. In addition, another study involving the discontinuation of tamoxifen (trade name NOLVADEX), used to treat breast cancer, concluded that approximately 88 out of the 516 participants decided not to take medication after two years of the study. This was also accompanied with a negative belief towards the medication and a positive status towards discontinuation.

Another consequence of noncompliance is the rise of drug-resistant bacteria. Because patients do not usually take medication as directed, incorrect habits form, which threatens the patient in addition to the population. Common behaviors of taking premature, sporadic, or intermittent halts in antibiotic regimens in addition to administering higher doses of medication in the beginning of the treatment regimen leads to resistant bacteria. Because of sporadic or intermittent noncompliance, drug resistant diseases develop. An example of this includes the case of tuberculosis. Because of non-adherence, patients who now contain the "secondary drug resistance" are able to occasionally transmit disease from one patient to another—which creates not only sets a panic to look for a stronger drug to kill the disease, but infects medical personnel and patients as well—creating more sick patients and therefore, increasing hospitalization. In addition, children are more vulnerable due to their compromised immunities. This is represented in the following case study: When a patient using antiretrovirals decided to take medication intermittently instead of everyday due to the fact that he could not afford the copay for the medication, he unknowingly becomes resistant to the medication. With the advent of superbugs, it is especially important to lower noncompliance rates of newly developed drugs, as if resistance of these drugs can lead to a loss of many lives and endanger the general population as a whole.

The most important and common consequence of medical non adherence is that healthcare professionals lack knowledge or data regarding the adherence of the patient. An analogy is a wall between the patient and the doctor, whereas ideally, the doctor should be able to directly interact with the patient during the treatment regimen instead of using a somewhat qualitative approach to determine patient compliance data. Such a qualitative approach includes doctors depending on the patients to do their part, taking their medication. However, not only has it been shown that the majority of the population does not take their medication as directed, but doctors cannot receive evidence denoting the fact that the patient is taking their medication; simple word of mouth is not enough to determine whether the patient is compliant. This negatively affects doctors, who do not know why the patient is not healing.

Although noncompliance can lead to many consequences such as an effect to hospitalizations and clinical trials as well as antibiotic resistance, the reason behind noncompliance is still debated among researchers. Noncompliance comes in two different types: intentional and unintentional. Intentional noncompliance is the action of deliberately not taking medication at all or as prescribed by a health personnel. This is usually a decision made by the patient while weighing the potential benefits and harms when taking a drug. Side-effects and drug dependency may take a role in such a decision. This is due to three reasons: a lack of knowledge on the potential advantages or disadvantages when taking another medication, when the phenotypic benefits of the treatment is either not visible, or not obvious, and the physiological adaptation needed to sense the need of help or treatment. First of all, patients do not have much of a context as to how the medication will change their daily lifestyle. Clinical records simply show adverse life-threatening reactions, but never display the change in the quality of life for the patient. Because of the faulty appraisal of the medication, negative side-effects become not only an unpleasant surprise to the patient, but also taking medication becomes a burden that the patient is now unwilling to take. For example, if a doctor prescribes a new drug to a patient with a certain illness, he/she will tell the patient that the medication will "cure the illness", and help the patient in that sense, but will not tell the patient of a possible unpleasant side-effect such as getting headaches; which leads the patient to think negatively of the drug itself. Secondly, benefits of a certain drug are not visible to the patient. In the previous example, the patient may not know that his/her illness is being cured, due to a lack of phenotypic difference by the drug. Instead, the patient phenotypically experiences the side-effect, once again giving a negative envisioning of the drug itself. This is fairly common on drugs which do not have a cure guaranteed for the patient, which would lead to a questioning of the effectiveness of the drug, especially if it produces side effects without a visible benefit. Table 10 displays this common, but incorrect perception.

Finally, the prospect of adapting to the fact that a patient is ill is based on the physiology of grief—in which the patient does not comply to the medication due to the fact that he or she may not want to be viewed as or view themselves as ill or sick. In addition, other unrelated issues that may cause grief may cause non-adherence. This is further exemplified in the following case study:

A 54-year old lady had a kidney transplant done when she was 24, and was in a very healthy state, and married a year after her transplant. However, after her husband passed away from a recent heart attack, she fell into a deep state of grief, which led her to temporarily stop taking medication due to her grief.

This shows how depression, although regarding a completely different issue, may affect non adherence.

However, the most important factor causing intentional non-adherence is the fact that medication is much too expensive to the average patient, and the cost of pills are increasing at a very drastic rate. For example, the costs of cancer drugs have been increased from $5000 to $10,000 before 2000, and over $100,000 in 2012. BIOGEN IDEC®'s drug for multiple sclerosis costs $54,900 per patient every year, in addition to Hepatitis C drug costs of $84,000 and Cystic Drug costs of $25

With the average income per person being approximately $51,000, such medication is definitely unaffordable by the general public. This induces medical non-adherence because it changes one's attitude towards the medication, causing him/her to behave adversely. These behaviors include taking pills every other day, taking half a pill every day, or simply taking medication when the illness is strong. Approximately 32% of older patients take less medication than prescribed to avoid high costs. This is done by either sporadically taking medications, especially when pain is received, splitting pills in half to make the prescription last longer, or delaying refills. This halts or delays the healing process, leading to ineffective and inefficient care. In addition, patients also simply discontinue the treatment. This is exemplified in which 15% do not fill out a new prescription. Out of those who do, 50% discontinue using the medication after six months, which creates major losses in the pharmaceutical industries (Table 12).

However, intentional non adherence is definitely not as drastic of a problem as unintentional non-adherence.

Unintentional non-adherence is a more significant and widespread problem in comparison to intentional adherence. Unintentional non-adherence is the result of the patient is willing to adhere to his/her prescriptions but is unable to do so due to obstacles that cannot be controlled by the patient. This includes not being able to recall whether medication has been taken, or not being able to find the medication, etc. Such a problem is very detrimental to pharmaceutical industries as well as other medical industries. In a study involving approximately 24,000 subjects, approximately 62% forgot to take their medication, 37% ran out of medication, and 23% were simply too careless. This is in comparison to only 33% who decided not to take medication intentionally. Unintentional non-adherence involves many different factors, such as age, race, gender, education, etc.

The first factor that will be discussed is age. Age plays a significant role in the elderly population because of the many challenges that they have, such as physical and mental disabilities. Studies show that approximately 40 to 75% of the elderly population do not take medication at the proper time, or the correct amount of medication required due to consequences such as a decreased cognitive and/or physical abilities that are present in higher rates in a younger adult. This is illustrated in Table 13.

In addition, elderly noncompliance accounts for approximately 26% of hospitalizations, and 25% of preventable adverse drug reactions. Finally, elderly noncompliance has caused a waste of billions of dollars in the healthcare industry. However, disputes have occurred based on whether age is a true contributor to noncompliance. For example, in a study based on fecal occult blood screening, compliance was at its peak for ages near 70, but slowly decreased at 80 years of age and 55 years of age.

A second factor that will be discussed is gender. Although there may not seem much of a difference between non adherence rates of men in comparison to women, associations do exist between gender and compliance. For example, women 27% are more likely to be non-adherent than men. Although research has not yet provided a transparent line as to why this tends to happen, explanations have been provided by researchers for this reason. These speculations include the fact that women are perhaps more price-sensitive to paying for out-of-pocket medication, or having a different level of health literacy, which is one's ability to process health information. On the other hand, studies also show that males are related to poor adherence. In one such experiment, males were 15% more non-adherent than females. Although these contrasting studies have yet to be confirmed, gender remains to be a significant factor for noncompliance. Distinctions of proper medication intake in males and females occur by as much as 10%.

A third factor that will be discussed is race. The relationship between race and noncompliance is widely studied among scientists. Caucasians are more likely to have better compliance than Blacks, Hispanics, and other minorities. Although there has not been a consensus behind why this occurs, a plausible explanation may be due to socio-economic barriers and language barriers in these minorities.

Multiple solutions will take place in response to problems stated above. The first solution to the immense problem of medical non-adherence is education. By having the knowledge and understanding the logical reasoning behind taking medication, patients can start increasing their personal rate of adherence. By utilizing education, intentional non-adherence is now decreased due to the fact that the patient will understand that although the cure will not be phenotypic, the medication is benefitting the body. In addition, by educating the public, new financial priorities may be set by the patient after considering the now-learned consequences and dangers of non-compliance. By prioritizing one's finance, the patient is able to pay off medication bills. Behaviors such as taking half a pill, or simply disregarding prescriptions may be nonexistent. Speculations behind the actual benefit of educating the non-adherent populations have been confirmed with numerous studies. For example, in a specific study, diabetes self-education program was tested to examine whether testing would lead to higher adherence rates. The results showed that approximately $415 can be saved by each patient who completes the education program (approximately 12 hours), over the span of three years. Over ten years, it is estimated that there would be a 12% decrease in coronary heart disease events, in addition to a 15% decrease in microvascular disease events.

Education also helps diminish the problem of health illiteracy—a significant problem in healthcare today. Defined as the ability for a patient to obtain, access, and understand health information and services to make appropriate health choices, health literacy has become a significant problem for patients and healthcare providers over the recent years. Approximately only 12% of adults have proficient health literacy. In addition, only 33.3% are able to do menial tasks properly, such as following directions on the prescription. Health illiteracy then becomes a concern because of the fact that the patient may not be able to determine when he/she has to take their medication. In addition, poison warnings or other hazards will not be read or understood, leading to hospitalization or a more extreme event—death. This also leads to shame of a patient, in which the patient is too embarrassed or ashamed to ask for help. In a study, approximately 85% of those who were illiterate did not admit it to their coworkers, and 50% hid their illiteracy from their children. An important factor in health literacy is numeracy. Being the ability for one to understand numbers, this factor is crucial to understanding health information. However, in this field itself, numerous patients struggle to comprehend simple numerical data. Studies show that 16% of highly educated individuals were unable to determine which has a higher risk: 1%, 5%, or 10%.

Education is also associated with the perception in which the patient is in control. In this case, by letting the patient receive the power to make his or her own choices, he/she is then actively participating in the pathway for successful drug compliance. Examples such as allowing the patient to decide when to take medication over having the doctor of pharmacist make decisions for them. Therefore, if the patient prefers taking medication in the morning over the evening, there is a higher probability of adherence in the morning rather than if the pharmacist forces the patient to take medication at night. In addition, medical personnel can also determine the motivation of the patient to cure their ailments, and determine adherence predictions before the patient takes medication. In conclusion, the multifactorial solution of education is able to limit the outbreak of intentional noncompliance in addition to unintentional noncompliance.

The second solution is to promote effective communication between the doctor and the patient. Studies show that poor communication with one's healthcare provider is linked to patient noncompliance. In addition, a study showed that compliance of the patient increased when the doctors are emotionally supportive, and provide empathy towards the patient. It is important for this to happen, as miscommunication can reduce transparency between the doctor and the patient, which usually occurs with multiple medication prescribers. It is shown that patients with multiple physicians and healthcare providers prescribing multiple medications tend to lose confidence in their health regimen. To solve such a problem, patient empowerment is needed. By allowing the patient to actively participate in the health regimen, doctor and patient communication occurs without hesitation by the patient. In addition to empowerment, it is important for patients to share all fallacies in their regimen to their physicians. For example, it is common for patients to admit to noncompliance when prompted, as exemplified in the case study. As displayed on Table 14, this also creates an ill-transparent disparity between the patient and the doctor. As shown in the Table 14 below, patients do not reach the ideal medical practices region, creating a gap between the patient and the doctor.

The third solution is to create an effective reminder system, one that is able to remind the patient to take their medication in addition to maintain compliance of the patient. As established above, unintentional noncompliance is most prevalent due to the fact that patients tend to forget to take their medication. Commonly found in the elderly sector, it is imperative to solve the overarching problem of carelessness and forgetfulness of patients. Reminder systems are effective because they allow the patient to not only take the medication that is required for their health regimen, but also allow the patient to get habituated in taking medication regularly. These reminder systems are only effective, however, if patient contact is at its highest. Therefore, it is important to understand the patient, and accustom the reminder system to how the patient communicates with his/her environment.

To be able to increase communication and prevent unintentional compliance, it is suggested that effective use of technology will be the most cost-effective and efficient to improve the healthcare system. With the coming of the twenty-first century, multiple devices and gadgets can be used in the healthcare system to reduce medical noncompliance. Technology is a very viable instrument that the system can use as it is very inexpensive, but is also very effective in enabling adherence. With the coming of new robots and wireless devices, the idea of using technology is more appealing than ever. However, the technology being implemented in the medical industry today is outdated, and has many flaws, making it less applicable in the 21st century.

One such technology utilized by pharmacists is the use of databases to allow for automated reminders to take medication though automated text messages, emails, and calls. Information regarding the date and time of automated messages would be received by computing metrics based on MPR data—involving the amount of days the patient had access to his or her medication. However, such technology is very inefficient and not beneficial. In a study involving 398 patients, using automated reminders along with monitoring devices did not show any significant benefit to medical adherence. Another study has also showed similar results—in a study with 275 patients, no significant benefit occurred with interventions such as automated and personal phone calls. Such use of technology is not very successful in healthcare today because of multiple factors. First, any benefits in adherence is only intended towards the patient, whereas doctors will not know the health regimen for the patient in terms of adherence. At the same time, pharmacists do not know for sure how many pills the patient took in a select time period. Because of this, neither doctor nor the pharmacists know whether the patient took the medication or not. This leads to the second flaw: the method is not flawless. Instead, it is far from determining actual adherence. Patients can simply decide not to take medication without notifying the doctor or the pharmacist, in addition to ignoring or subscribing to stop automated reminders. When these two effortless procedures are taken, the database is simply useless. Finally, automated reminders are simply not effective in reminding patients to take medication. Reminders can be simply ignored by the patient, and also, the patient can simply turn off reminders from pharmacists (As daily automated reminders can be irritating to some). Therefore, databased, and automated reminders and adherence predictions are not effective due to its impracticalities.

Another form of technology involves writing prescriptions, called e-prescriptions, in which prescriptions are written electronically rather than by hand. This makes a major difference because handwritten notes are easily misplaced by patients. In addition, handwritten notes do not provide any verification that the patient came to pick up his or her medication. This behavior usually goes unseen because pharmacists are not aware of the fact that the doctor has prescribed medication to a specific patient. By using electronic prescriptions, pharmacists are able to verify and determine whether certain medication is supposed to be picked up by the specific patient. Also, refills of medication under the awareness of the pharmacist can counter patient forgetfulness to take medication again. Unlike automated phone calls by database-related pharmacies, e-prescribing has led to a benefit in terms of the amount of prescriptions filled (as shown in Table 15).

However, it does not solve the entire problem. There are still many aspects of noncompliance not covered by the idea of e-prescribing. First of all, although there is an increase of prescription pickups, e-prescriptions do not affect the aspect of patients taking medication at home. Secondly, errors occur between pharmacist and doctor communication (due to software problems) which would lead to decreased efficiency. Approximately 1 out of every 10 prescriptions sent result in pharmacist intervention because of a lack of specificity or other complications. More importantly, however, is the cost of such technology. Per prescriber, the cost is approximately 2,500 dollars, too expensive for the average physician. Although electronic prescriptions are helpful to some degree in decreasing noncompliance, its expenses are simply too high for a practical solution.

Although one can see the flaws in the multiple outdated technologies above, the idea of using technology is not diminished Instead, new technology is implemented to create the items found in a patient's daily life "smart", meaning that they have enhanced features to accommodate for noncompliance. The most effective of these is the pill-bottle, which is simply the remodeling of the standard pill bottle found in pharmacies into one that is able to do much more than serve simply as a container—a "smart" pill bottle. They are especially beneficial because of the fact that a patient (ideally) is in contact with a medication bottle frequently. Due to this fact, it is easier, and more effective to create the "smart" component in a pill bottle over other medication interactions. An example would be creating a pill bottle that can also remind patients in addition to holding medication.

When discussing L-shaped elbowed hollow aerosol inhalers, we must acknowledge the important factors needed in an inhalation device, which can be a daily dosage inhaler, such as Dulera®, or it can be a rescue inhaler, such as ProAir® or Ventolin, to be used to abate a random but dangerous asthma attack. By looking at the analysis above, it is determined that the following factors/problems/solutions must be addressed in an L-shaped elbowed hollow aerosol inhaler: communication between doctors, respiratory therapists and patients, reminder systems in the elderly and pulmonary deficient population, cost-effectiveness in the device, decreased inefficiency of the patient and the doctor, and flawlessness. Before discussing how an improved L-shaped elbowed hollow aerosol inhaler successfully achieves these factors, it is important to see how other L-shaped elbowed hollow aerosol inhalers bottles are designed, and the flaws in their device.

For example, a typical aerosol rescue inhaler has a meter showing how many dosages have been used, but it does not communicate this information to a health care provider in a real time basis. The same situation is true with the Dulera® daily dose inhaler.

As seen in these top-market L-shaped elbowed hollow aerosol inhalers, the devices are not reliable because they do not communicate remotely via wireless Wi-Fi or Bluetooth® remote communications. Nowhere in the market can one see a device that is beneficial also to the doctors and the pharmacists in conjunction to an effective communication between the doctors and the patients. In addition, most of the devices that are available in the market tend to be too expensive for the common patient.

OBJECTS OF THE INVENTION

The inventive L-shaped elbowed hollow aerosol inhaler of the present invention is able overcome the shortcomings of the known art, including solving one or more problems in medical noncompliance at a very low price.

In contrast to aforementioned prior art L-shaped elbowed hollow aerosol inhaler and dispensing devices, the present invention is an L-shaped elbowed hollow aerosol inhaler compliance device that functions to satisfy important dosage communications in medical noncompliance at a very low price.

It is also an object of the present invention to provide an L-shaped elbowed hollow aerosol inhaler device which can detect adherence and non-adherence of a pulmonary medical patient's pharmaceutical treatment regimen, which utilizes detectable signals which can be transmitted via a Smartphone or via a Wi-Fi connection to the Internet to the Cloud storage media, without a separate dedicated signal transmitter and which promotes pulmonary patient adherence to his or her treatment regimen.

Other objects will become apparent from the following description of the present invention.

SUMMARY OF THE INVENTION

What separates this invention from other devices is two major things: a) it is much, much cheaper than the current market; and (b) it is able to accommodate for a lot of inhalers, whereas other inventions tend to only adapt to one type of inhaler.

The mechanism the inhaler uses is the same as the other invention—it has a chip that connects to the patient's Wi-Fi network, and sends data to a web server (I have now created a website that receives the data). This data that is sent is completely encrypted, so that patient information is not lost. The name of this IoT device that sends this data is called the ESP8266 ESP-12E. IT is a Wi-Fi chip that is able to send out this data. The device has a rechargeable battery (more specifically a 150 MaH LIPO Battery) inside of it. The battery is connected to the printed circuit board (called the PCB).

The sensor itself is called a reed switch sensor. There will be a magnet that is attached to the cap of the device. When the cap is opened, the reed switch will detect the distance the magnet is from the switch. Given a threshold, the sensor is able to detect whether the patient has opened the cap or not. Once detected, the adapter will send the data (that the patient has taken the medication) to the web server through the use of Wi-Fi.

The present invention is an adapter that can essentially bind 90% of existing asthma inhaler devices and detect whether the patient has taken their medication. The adapter can determine this by detecting whether the patient has opened the cap of the inhaler (which is used to allow the patient to take his/her medication).

The L-shaped elbowed hollow aerosol inhaler compliance device is able to fit the objects and criteria established above. The phrases "aerosol inhaler", inhalator aerosol dispenser, "HFA inhaler" and "device" are used interchangeably herein to describe the inventive L-shaped elbowed hollow aerosol inhaler device. The aerosol inhaler is able to accomplish this by the utilization of two major components: the device itself, and a smartphone app. The compliance aerosol inhaler involves three parties—the pulmonary patient who will simply use the device similar to that of any other aerosol inhaler, the doctor, or other medical provider who will be able to see the compliance, and the pharmacist information.

To briefly summarize the process, first, the inventive aerosol inhaler is activated with the removal of the mouthpiece cap from the L-shaped elbowed hollow container in a housing with an output spout. In addition, the “smart” feature of the device is also activated. By removing the mouthpiece cap, a Bluetooth® or other wireless signal is sent from the device to a companion smartphone app. The app recognizes that the mouthpiece cap has been removed to release the aerosol dosage. The app itself will receive the signal, and calculate the date, time, medication, and other necessary information. With this data, the app connects remote spreadsheet tabulation, such as GOOGLE® sheets document in the patient’s GMAIL® account, and adds the information to the next row. The GOOGLE® sheets can then be shared with pharmacists, doctors, and other medical personnel. By using a GOOGLE® sheets account, the healthcare providers are able to create charts, data tables, etc. to accommodate to their needs.

This application first discusses the inventive L-shaped elbowed hollow aerosol inhaler compliance device itself. That is, the L-shaped elbowed hollow aerosol inhaler dosage compliance device will be discussed into two separate parts: Physical components and Software components. The physical components will first be discussed.

The main physical component in the inventive aerosol compliance device is a microcontroller on a circuit board that contains multiple electronic components, in addition to the microcontroller, such as memory, voltage regulators, switches, sensors, pick-up devices, and a Bluetooth® module, etc., as known to the skilled person. The microcontroller includes a programmable processor or CPU along with memory and programmable input/output devices. In the alternative, the main physical component is a system on a chip (SoC), which includes a microcontroller as one of its components. The present invention uses the circuit board and components, or SoC to process any code or instructions programmed into and/or received by the entering the L-shaped elbowed hollow aerosol inhaler dosage device, and to process signals from user activation, to send one or more signals to the Bluetooth® module or Wi-Fi module (which will be discussed herein later), that are in communication with the L-shaped elbowed hollow aerosol inhaler dosage device.

The microcontroller, whether on a circuit board of SoC may be programmed by accepting code via a USB port. In other words, the microcontroller is able to be programmed by a computer or computer server through a simple USB connection. To facilitate the USB connection, a USB compatible port can be provided a wall of the portion of the device having the electronic components therein, such as, for example, within a the attachment housing which wraps around the L-shaped elbowed hollow aerosol inhaler dispenser device housing, which includes a barrel having the pressurized container of gaseous respiratory mist products therein, such as, for example, albuterol sulfate. This is important because of the fact that it does not need additional circuits to program the device. Any errors in the device can simply be fixed by a re-insertion of the code itself. Finally, the microcontroller, whether on a circuit board of SoC has a power input at (preferably soldered into) the circuit board, that also may operate to charge a battery. Preferably, the battery is easily replaceable and battery types can easily be found in stores. Both features are especially important for both the patient and the pharmacist because of the fact that troubleshooting is very simple to accomplish—it simply takes one to reset the code with a USB cable to restart the device once again. At the same time, patients have the option to have rechargeable batteries, which simply need to charge for a short time before proper functionality returns. One example of a power source battery is an 1800 MaH LIPO battery, or an equivalent power source battery, which is connected to the pcb (PC board).

The second most important component of the inventive L-shaped elbowed hollow aerosol inhaler dispenser compliance device is the Bluetooth® module. Such a module is important in communicating with the smartphone app from the device. In one embodiment, communication from the L-shaped elbowed hollow aerosol inhaler dosage device is carried out using Bluetooth®, a standard for transmitting and receiving signals within short distances (10 meters). In this first embodiment, Bluetooth® is preferred over other signaling types such as radio, Wi-Fi, etc., because Bluetooth® is able to ease communication between the ANDROID® app and microcontroller, whether on a circuit board of SoC. Secondly, unlike Wi-Fi, Bluetooth® can be used in areas where Wi-Fi is not available, and is convenient when travelling. Finally, Bluetooth® is a very inexpensive form of communication—as the Bluetooth® module costs approximately one dollar. The Bluetooth® module itself is preferably a low-power transmitter, in which battery power is not used significantly—this allows the battery to last for a significant amount of time.

However, in a second embodiment, a reliable Wi-Fi module can be used for communication between the device and Smartphone. The Wi-Fi module preferably is a Particle Photon IoT unit Wi-Fi module or router. In a second embodiment, the Wi-Fi module or router receives a signal from the device and sends the received signal through a user computer electronically connected to the Wi-Fi module or router (for example, via the user’s browser) via the Internet either directly to a Cloud storage media, or to a server that reroutes the received signal to the Cloud storage media. The user signals are privately stored in the Cloud storage media where they may be retrieved by authorized personnel, such as a patient's treating physician, also over the Internet. While not being limited, in one example, the IoT microcontroller may be an ESP8266 Node MCU.

In yet another embodiment, the inventive inhaler compliance device is in the form of an L-shaped elbowed hollow aerosol inhaler dispenser device with the driving electronic (such as a switch, electronic control, and communications components) housed completely in the housing. In this embodiment, Bluetooth® communication and a cell phone are not needed since the microprocessor module selected has wi-fi capability and directly communicates to cloud storage in this manner. Either a rechargeable cell such as a Lithium polymer (LiPo) cell or a replaceable primary cell may be configured to power the electronics (also maintained in the cap). The intended operation (i.e., aerosol dosing) is detected recorded by the inventive L-shaped elbowed hollow aerosol inhaler dosage device once the mouthpiece cap is removed and then returned to the device. Although a mechanical switch can be used to detect pulling off and then returning the cap, a switch printed circuit board (pcb) with a capacitive touch sensor and a floating ring and a press pad is preferred.

The switch and electronic communications components are housed in the L-shaped elbowed hollow aerosol inhaler housing, or strapped adjacent thereto, and activated by a twist-off movement of the cap. Once push down of the pressurized aerosol container is detected, the inventive device alerts the person (in the future) through email or iPhone messages rather than contemporaneous sound/visual alerts from the device. The sensor that detects the pushing down and aerosol dosage has occurred, a compliance circuit is completed. A charge would then power the device. The charge serves as a detectable event. The power is preferably supplied by the battery/super-capacitor.

The press plate senses and the removal of the mouthpiece cap, and a super capacitor is deployed to harness energy from a battery cell and supply it to the microprocessor, such as, for example, an esp8266 Wi-Fi board. The energy for the electronics is stored in the capacitor, and the energy comes from the battery to the capacitor, rather than just coming directly from the battery. The function of the capacitor is to be able to supply the large current needed by the esp09 microprocessor module. If the user tries to draw 70 ma of current from a battery in such a short time, the battery will die within hours. However, if the user can take this current from a capacitor (which can supply current quickly), the battery can slowly recharge the capacitor without losing its capacity.

The inventive device is directly connecting to Wi-Fi, obviating a need or a smartphone app receiving software receives data from the inventive L-shaped elbowed hollow aerosol inhaler compliance bottle (device), which can optionally be GOOGLE® or other databases, a web portal, or an IP address that receives patient information. That is, this embodiment of the inventive L-shaped elbowed hollow aerosol inhaler dosage compliance (device) utilizes a website to display data to the patient, pharmacist, and physician in an intuitive way. The receiving software is able to integrate with the patient's current EHR (electronic health records), regardless of its physical or electronic location (e.g., across the country). The software stored in a memory and operational in a microprocessor or the like included in the electronics. is compatible with many current hospitals and physician's systems that rely up EHRs physicians.

The inventive L-shaped elbowed hollow aerosol inhaler compliance device is user activated. It implements this function in any number of ways, for example, using a switch, that detects each mouthpiece cap removal prior to pushing and dispensing of the aerosol mist, the removal of which is detected to cause activation of the wireless signaling components (by a switch located near the other electronic components).). The device component is able to generate a digital signal when the mouthpiece cap is removed. The signal is preferably stored either in a buffer or in some other type of memory storage element. In a preferred embodiment, the removal switch will send approximately one byte every time to the microcontroller is pressed (actuated). Although it is very simplistic, it is key to determining whether the patient has taken the aerosol medication or not.

At the same time, extensive technology such as infrared sensors, etc., to detect whether the patient has taken his/her medication because of the fact that extensive additions can increase the price of the device by a significant amount, and are also too large to practically insert in the device. However, future devices may have these additional features.

In an embodiment, the invention provides an L-shaped elbowed hollow aerosol inhaler dosage compliance device for maintaining a patient's aerosol dosage supply and monitoring the patient's access to the aerosol mist dosage contained in the device to memorialize the patient's compliance with his/her inhalation-taking regimen. The device comprises a housing, including an inner pressurized aerosol container storage compartment and an electronics unit, a removable mouthpiece cap covering mouthpiece compartment of the housing, including a switch to detect removal of the cap to detect a completion of metered dosages in a transition from an active state, to a dormant state, when the switch is proximate due to the movement of the storage container in the housing mouthpiece cap from the aerosol and triggers a transition from the dormant state to an active state.

A transition from the active state to the dormant state, by removal of the cap generates an access signal; a transition from the dormant state to the active state, by replacing the mouthpiece cap to the housing generates an aerosol dosage-taken signal. If the dosage-taken signal is generated within a predetermined period after the signal is generated, the microcontroller generates a compliance notification signal that is communicated to a Wi-Fi module or router within or attached to said electronics unit, to memorialize the apparent compliance. The Wi-Fi module or router may direct the notification signal to an Internet address or URL of a medical service provider or cloud storage system, where the user data of the Wi-Fi notification signal is stored and accessed by authorized users. A failure to send a Wi-Fi notification signal to the medical service provider within a "failure to take" period results in an automatic communication to notify a $3^{rd}$ party that the user has failed to take a required inhaler respiratory medicine mist.

The electronics unit may be located in a side compartment adjacent to the housing or as part of the housing, or in a side portion of the housing adjacent to said inner pressurized storage dispenser.

The invention also provides a microcontroller-controlled method of providing aerosol dosage compliance for maintaining a patient's aerosol dosing supply and monitoring the patient's access to the aerosol dosages contained in the device to memorialize the patient's compliance with his/her inhaler-taking regimen. The L-shaped elbowed hollow aerosol inhaler compliance device comprises an electronics unit with a microcontroller and electronic components such as memory, a housing with an inner pressurized dosage compartment for storing the aerosol, a removable mouthpiece cap covering mouthpiece and a switch to detect removal of the cap, wherein a switch triggers a transition from an active state, to a dormant state.

The method includes steps of first generating an access signal upon removal of the cap from the dispenser container in the housing where the access signal is indicative of a transition from the active state to the dormant state. The microcontroller generates a compliance notification signal and provides said compliance notification signal to a Wi-Fi module or router within, attached to or coupled to the electronic unit to memorialize the apparent compliance. For that matter, the step of the microcontroller generating a compliance notification signal includes directly sending the signal to a $3^{rd}$ party to communicate that the user has failed to take a required metered dosage, and may further include sending said signal to a cloud storage system, where the user data of the Wi-Fi notification signal is stored and accessed by authorized users. The step of the microcontroller generating a compliance notification signal requires generating a signal within a predetermined time period; the access signal indicates the time and date that a patient user acted to obtain access to the aerosol mist to be dispensed from the L-shaped elbowed hollow aerosol inhaler dispenser device.

BRIEF DESCRIPTION OF DRAWINGS

The present invention can best be understood in connection with the accompanying drawings. It is noted that the invention is not limited to the precise embodiments shown in drawings, in which.

DETAILED DESCRIPTION OF THE DRAWINGS

Figure 1:
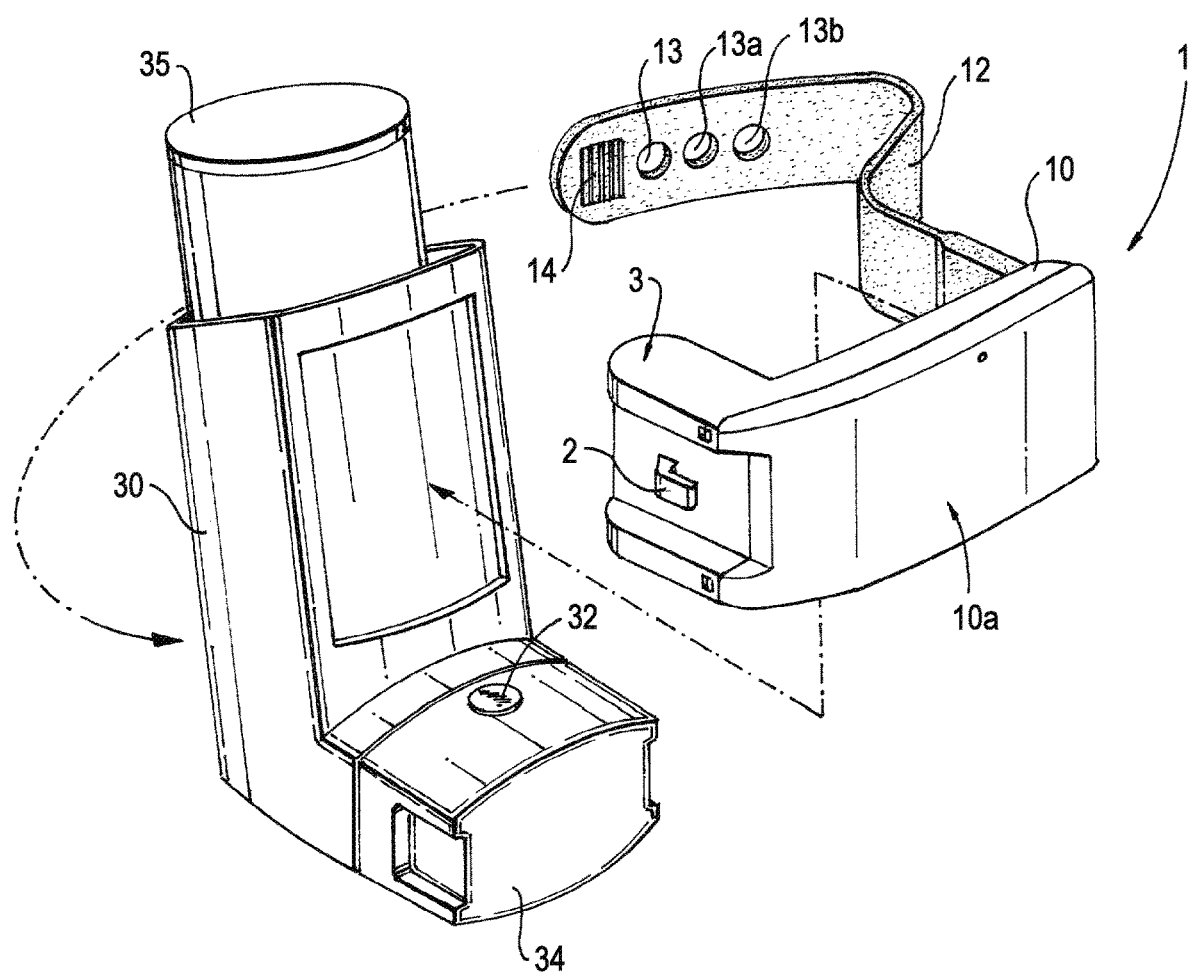
FIG. 1 is an exploded perspective view of an L-shaped elbowed hollow aerosol inhaler dispenser container of the compliance device, shown in place upon an aerosol inhaler dispenser container.

In the embodiment shown in FIGS. 1-4, the inventive L-shaped elbowed hollow aerosol inhaler dispenser container embodies a wraparound compliance device structure 1 that wraps horizontally around the L-shaped aerosol inhaler dispenser container in the vicinity of the elbow above where the mouthpiece 31 and cap 34 with a magnet affixed thereto, extend obliquely therefrom. Consequently, the mouthpiece 31 and cap 34 are cantilevered outward beyond the L-shaped elbowed hollow aerosol inhaler dispenser barrel storage compartment 30 retaining the compartment 35 of aerosol medicine, such as Pro Air albuterol or Dulera, for example, under pressure. The cap 34 with the magnet 2 of the mouthpiece 31 is removed from mouthpiece 31, so that the user can place the mouthpiece 31 into the mouth, wherein, upon user pushing of the aerosol containing compartment 35 down within the storage barrel 30, the mist of the aerosol is gaseous released into the mouth of the user. Therefore, in the present invention, removal of the cap 34 causes the electronics 6 (such as a Wi-Fi chip, i.e. ESP-12-E) in the chip housing 10 of the wraparound attachment compliance device 1 to send a signal to a health care provider that the user has removed the mouthpiece cap 34 to use the inhaler dispenser container 30.

A magnet 32 is located in the top lid portion of the mouthpiece cap 34, so that, upon the removal of the cap 34 from the mouthpiece 31, the magnet 32 is moved out of range from reed switch 22 located in the electronics storage base portion 10 of the wraparound attachment compliance device 1, which has a hollow region, including a platform support bracket (i.e. "stage" area) to hold a microcontroller module such as Wi-Fi chip 6, which is preferably an IoT device, such as an ESP-12E, to facilitate wireless communications. Indicator lights 9 shining through LED indicator hole 9a disclose whether the device is running, what code is used and if there are any malfunctions of the compliance device. 1

The wraparound attachment has a separate hollow battery housing 3 with battery 5 therein. The battery 5 connects by power cable wires and power connector 4 to the Wi-Fi chip 6. The battery housing extends angularly extending from the chip housing 10, so that the two housings 10 and 3 form a generally elbow configuration.

FIG. 1 shows compliance device 1 of this invention with wraparound strap 12 attached which has adjustment holes 13, 13a and 13b and embossed grip 14. Wi-Fi housing 10 is shown with battery compartment 3 at a right angle at the proximal end. Removable cover 10a is shown attached. Hook 2 engages with holes 13a-c to attach to inhaler 30 housing. Inhaler container 35 is shown inside inhaler housing 30 and mouthpiece cap 34 covers the mouthpiece.

Figure 2:
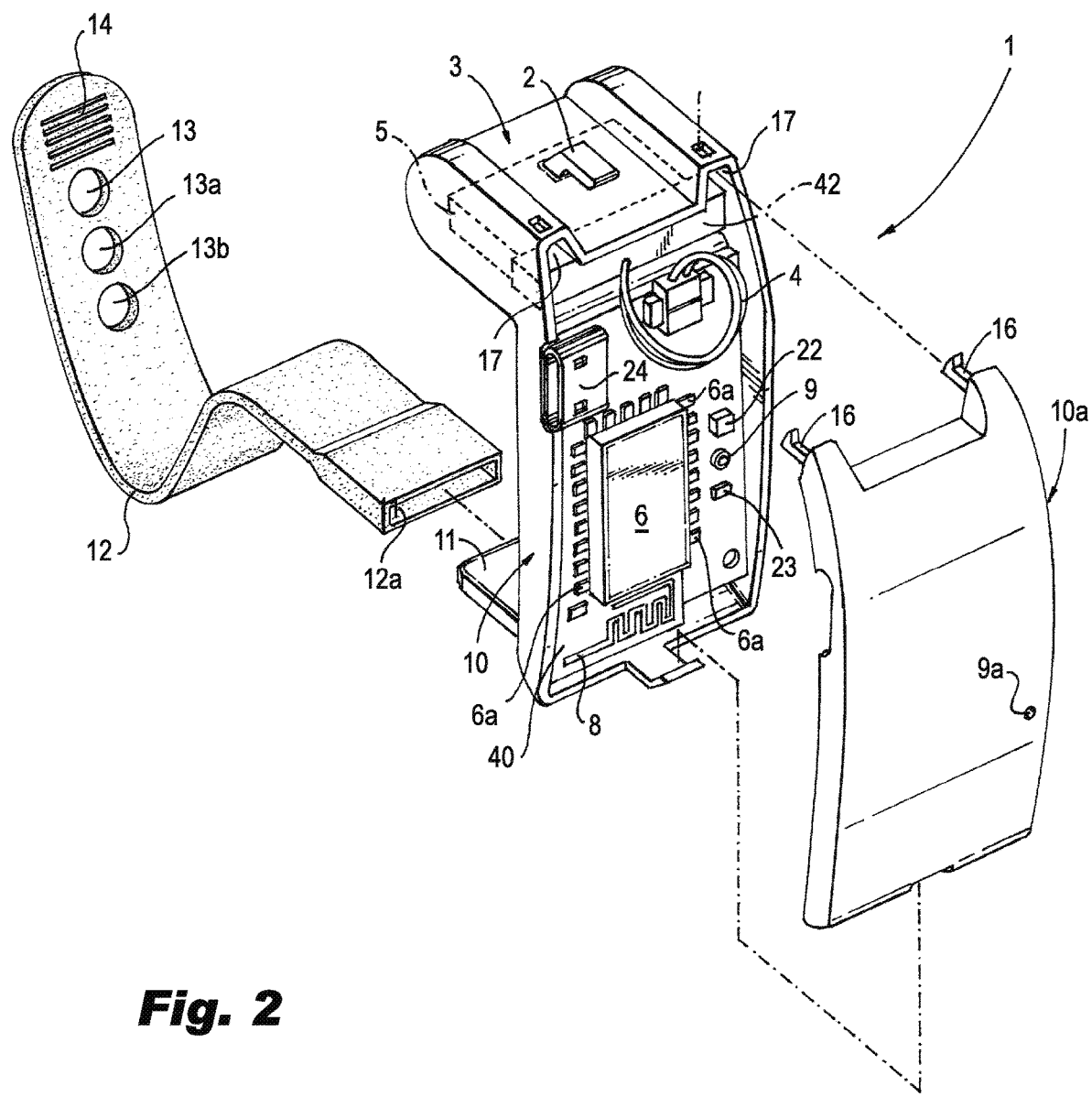
FIG. 2 is an exploded perspective view of the inventive L-shaped elbowed hollow aerosol inhaler dispenser container compliance device with its electronic components exposed upon removal of a housing cover of the L-shaped elbowed hollow aerosol inhaler container compliance device.

FIG. 2 shows strap 12 detached from tang 11 on housing 10 by virtue of coupler 12a being pulled away. Printed circuit board 40 has various components attached such as Wi-Fi processor chip 6 which is a surface mount module soldered at tabs or pins 6a. Also mounted are LED 9, capacitor 23 and reed switch 22. Power is introduced via cables and power connector 4. USB connector 24 is for both battery charging and downloading of operating software or updates. Cover 10a is hooked via hooks 16 into holes at 17 at the back top of battery housing 3. Hole 9a permits one to see the illumination from LED 9 which is in registration when cover 10a is closed.

Figure 3:
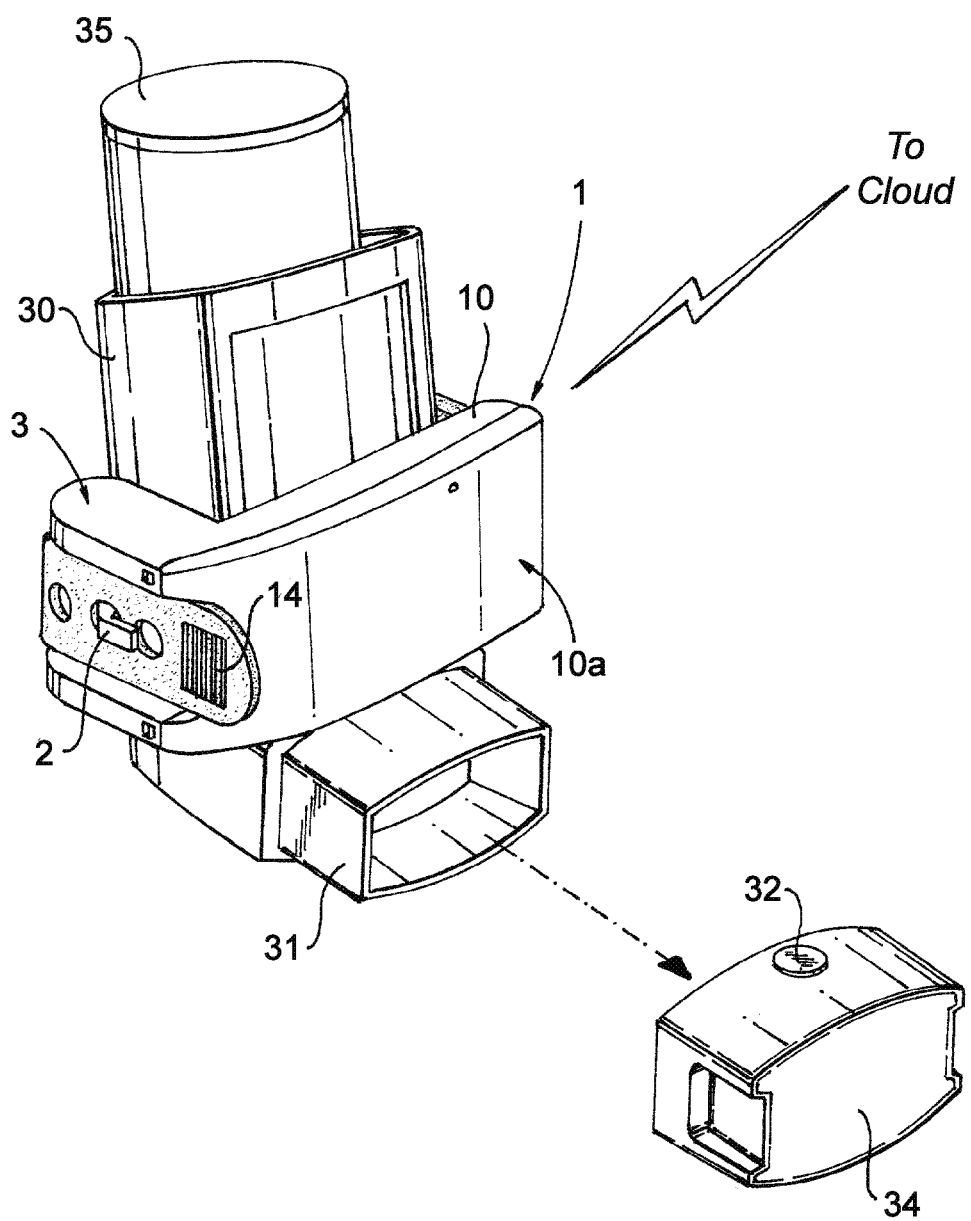
FIG. 3 is an exploded perspective view of the L-shaped elbowed hollow aerosol inhaler dispenser container of the compliance device, shown in place upon an aerosol inhaler dispenser container and with the mouthpiece cover of the aerosol inhaler dispenser container removed, whereby movement of a magnet located at the mouthpiece cover activates the electronics in the compliance device to indicate that the mouthpiece cover has been removed to partake of the aerosol dispensed from the aerosol inhaler dispenser container.

FIG. 3 shows the compliance device 1 of this invention engaged with inhaler 30 via strap 12 which preferably is elastic. Mouthpiece cap 34 is shown removed from mouthpiece 31 with the inhaler ready for use.

Figure 4:
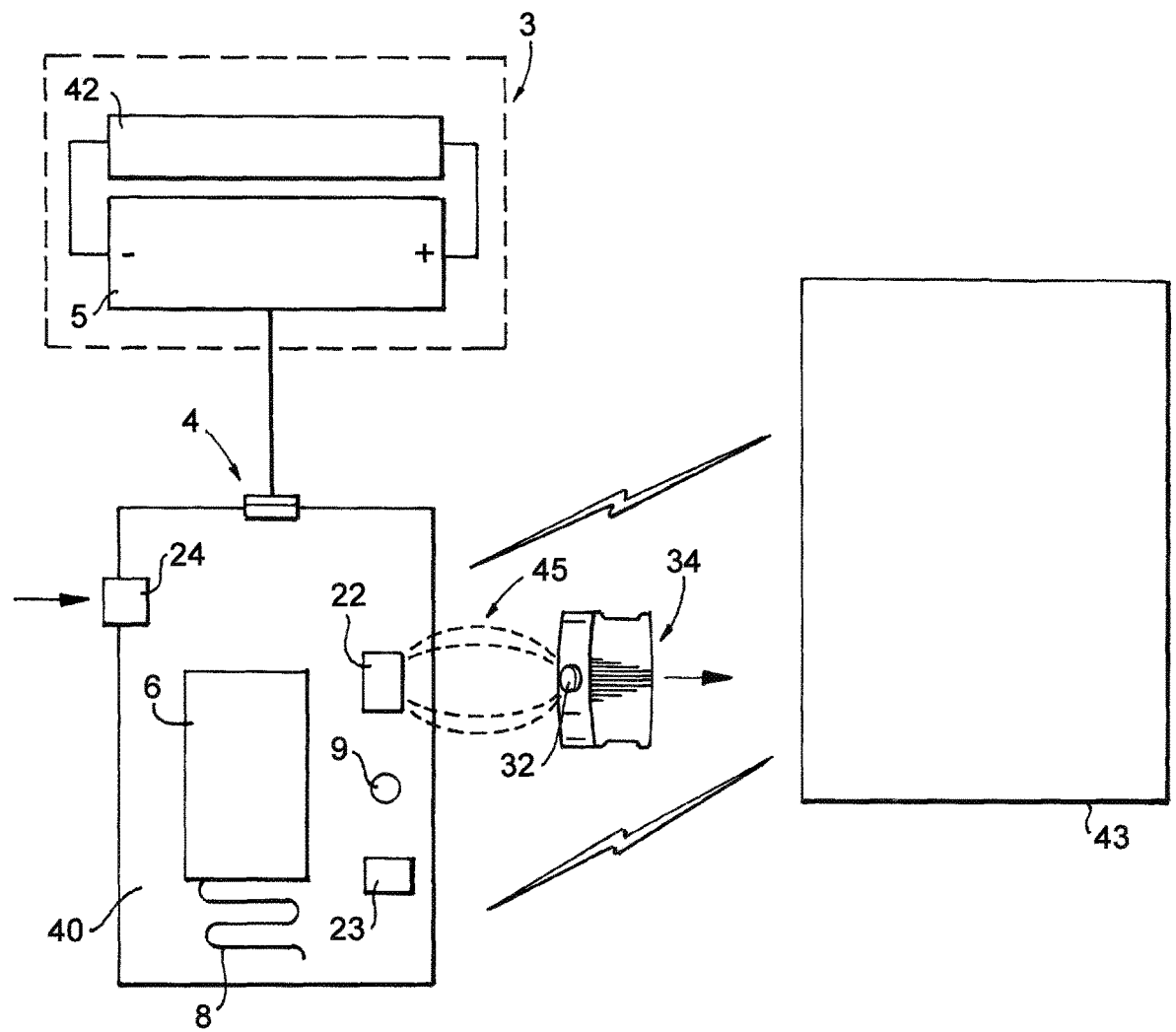
FIG. 4 is a block wiring diagram of the compliance device of this invention.

FIG. 4 shows a wiring diagram of major components. Battery compartment 3 houses battery 5 as well as supercapacitor 42. Power cable and connector 4 provides power to PCB board 40. In case battery 5 is a rechargeable type, these same cables and connector 4 would carry charging current to battery 5. USB connector 24 is also used for charging. Movement of magnet 32 atop mouthpiece cover 34 is detected by reed switch 22 via coupling magnetic lines of force 45. Communications to the cloud or nearby devices such as tablet or cell phone 43 is through Wi-Fi antenna 8.

The microcontroller Wi-Fi chip 6 includes a programmable processor or CPU along with memory and programmable input/output devices. Alternatively, the inventive aerosol dispenser compliance device embodied a system on a chip (SoC), which includes all the necessary electronic components mentioned above. The present invention uses the circuit board and components, or SoC to process any code or instructions programmed into and/or received by the entering the wraparound attachment compliance device, and to process signals from the reed switch, to send one or more signals to the Bluetooth® module or Wi-Fi module (which will be discussed herein later), that are in communication with the health care provider.

The microcontroller, whether on a circuit board or SoC, may be programmed by accepting code via a USB port. In other words, the microcontroller compliance device is able to be programmed by a computer or computer server through a simple USB connection. To facilitate the USB connection, a USB compatible port can be provided a wall of the portion of the device having the electronic components therein. This is important because of the fact that it does not need additional circuits to program the device. Any errors in the device can simply be fixed by a re-insertion of the code itself. The microcontroller, whether on a circuit board of SoC, has a power input at (preferably soldered into) the circuit board, that also may operate to charge a battery. Preferably, the battery is easily replaceable and battery types can easily be found in stores. Both features are important for the patient and the pharmacist because as they enable very simple troubleshooting—the inventive device simply takes one to reset the code with a USB cable to restart the device once again. At the same time, patients have the option to have rechargeable batteries, which simply need to charge for a short time before proper functionality returns. One example of a power source battery is an 1800. MaH LIPO battery, or an equivalent power source battery, which is connected to the pcb (PC board).

The second most important component of the device is the Bluetooth® module. Such a module is important in communicating with the smartphone app from the device. In one embodiment, communication from the L-shaped elbowed hollow aerosol inhaler dispenser compliance device is carried out using Bluetooth®, a standard for transmitting and receiving signals within short distances (10 meters). In this first embodiment, Bluetooth® may be used over other signaling types such as radio, Wi-Fi, etc., because Bluetooth® is able to ease communication between the ANDROID® app and microcontroller, whether on a circuit board of SoC. Secondly, unlike Wi-Fi, Bluetooth® can be used in areas where Wi-Fi is not available and is convenient when travelling Finally, Bluetooth® is a very inexpensive form of communication—as the Bluetooth® module costs approximately one dollar. The Bluetooth® module itself is preferably a low-power transmitter, in which battery power is not used significantly—this allows the battery to last for a significant amount of time.

However, in a third embodiment, a reliable Wi-Fi module can be used for communication between the device and Smartphone. The Wi-Fi module preferably is a Particle Photon IoT unit Wi-Fi module or router. In a second embodiment, the Wi-Fi module or router receives a signal from the device and sends the received signal through a user computer electronically connected to the Wi-Fi module or router (for example, via the user's browser) via the Internet either directly to a Cloud storage media, or to a server that reroutes the received signal to the Cloud storage media. The user signals are privately stored in the Cloud storage media where they may be retrieved by authorized personnel, such as a patient's treating physician, also over the Internet. While not being limited, in one example, the IoT microcontroller may be an esp8266 Node MCU.

Another component of the physical device is the user activated actuator, which is the removable mouthpiece cap with a magnet associated which with the magnet reed switch (or like device), where, the removable of the mouthpiece cap causes the magnet to pass the reed switch, which generates a signal (i.e., a detection of an opening or a closing), which signal then causes activation of the wireless signaling components. The signal is preferably stored either in a buffer or in some other type of memory storage element. In the embodiment with the removable lid with a reed switch sensitive magnet therein, approximately one byte is sent every time to the microcontroller is pressed (or otherwise actuated). Although it is very simplistic, it is key to determining whether the patient has taken the medication or not. To prevent accidental button presses, the button contains a resistor factor, which will add a certain amount of resistance when the removable mouthpiece cap is removed. Because of this, accidents such as toppling the L-shaped elbowed hollow aerosol inhaler dispenser device will not trigger the reed switch. The digital signal activating the microcontroller and wireless communication, is caused by removal of the mouthpiece cap therefrom, to move the magnet within the lid to be out of range from the reed switch, which is then activated to generate the digital signal.

The ESP09 module has an embedded ESP8266 processor plus wi-fi capability. A 70 ma draw from the bottom makes it prudent to also use the super capacitor and the resistor to smooth out the current in-rush with a resistor while storing a charge in the capacitor from the cell.

The PCB switch is one that conducts a charge when pressed upon. When forced upwards, it will complete the circuit and then activate the printed circuit board. It will not generate a new charge. It is called a PCB board switch, but technically it does not really have its own circuit—it is just a form of switch.

There is no pushbutton on the ESP09 module, since the only switch is the switch PCB. To make the switch work, the switch is activated and deactivated. As a result, when the patient removes the mouthpiece cap from the mouthpiece of the inhaler, the movable floating ring will move down, and the switch will be deactivated. The movable floating ring will be forced up, and will press upon the pcb switch. This will activate the electronic components of the ESP09 microprocessor module which send signals to health care givers that the patient has accessed the inhaler mist from within the aerosol dispenser container.

The problem with the battery cell is not the capacity, but the battery cell does not supply the necessary current fast enough. The 70 ma draw from the circuit can take away a significant amount of load from the cell battery. As a result, the supercapacitor is provided to accumulate the current from the battery cell over a short period of time, and discharge it fast enough to power the circuit board. The resistor is provided to control the discharge from the capacitor.

The signals can be set to a website, or to the GOOGLE® Sheets of a Google Docs spreadsheet.

The aerosol dispenser compliance device is a very viable solution to the problem of medical noncompliance. Not only can it effectively communicate compliance information to its healthcare providers, but it can also do this in a very low price. Given that the microcontroller can be received for approximately seven dollars, the Bluetooth® module can be received for approximately one dollar, and the push button, wires, etc. can all add to a negligible amount of money, one can determine a final cost of twelve dollars including the cost to 3D print the frame of the device. This cost is very affordable by the general population.

Future investigations would include creating a fingerprint-enabled device to first, prevent other users to take one's medication, an incident that is common over the recent years. By using a fingerprint, the patient is the only person who is able to open the device. Secondly, by adding a one-dosage control, overdose is prevented. By having the device only produce one set of medication, the patient is not able to access other sets, therefore preventing unintentional and intentional overdosage.

The aerosol dispenser compliance device is able to limit noncompliance in the US healthcare. By doing this, it has the potential to save billions of dollars in wasted money, in addition to drastically increasing adherence rates. Not only will this benefit the aspect of waste from not adhering to medication, avoidable hospitalization will decrease, in addition to lowering biases in clinical trials. Finally, an increased transparency will be ensured between the doctor and the patient, which will therefore boost the treatment outcome of the patient. With broader implications, body or microbe resistance can be decreased in addition to benefits of the patient, who's in-disease activity will be decreased. By realizing the meta-analysis above, it is also important for one to see the immediate need to solve the holistic waste of the healthcare system. The aerosol dispenser compliance device has this potential- to alleviate patient to doctor communications, and encourage the health regimen to allow the healthcare industry to care for our patients for today, tomorrow, and into the future.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. An aerosol inhaler dispenser compliance device for maintaining a patient's aerosol mist usage supply and monitoring a patient's access to aerosol contained in the device to memorialize a patient's compliance with his/her aerosol use regimen, said compliance device comprising:
    an L-shaped, elbowed, hollow container, including an inner aerosol barrel storage compartment and a removable mouthpiece cap for covering the L-shaped, elbowed, hollow container and the inner aerosol mist storage compartment; and
 a wraparound attachment;
    wherein said removable mouthpiece cap includes a power supply, a mechanical switch and an electronics unit including a microcontroller and a memory;
    wherein said mechanical switch includes a capacitive touch sensor element and a switch press element communicating with a press plate;
    wherein removing said removable mouthpiece cap from said L-shaped elbowed hollow container triggers said mechanical switch to an open switch state, generates and transfers an access signal to said microcontroller, and provides access to the L-shaped elbowed hollow container of said aerosol inhaler dispenser;
    wherein placing said removable mouthpiece cap on said L-shaped elbowed hollow container triggers said mechanical switch to a closed switch state, generates and transfers a no-access signal to said microcontroller, and prevents access to the aerosol mist; and
    wherein if a no-access signal is generated within a predetermined period after an access signal is generated, said microcontroller generates a compliance notification signal that is communicated to a Wi-Fi module or router within or attached to said electronics unit.

2. The aerosol dispenser compliance device of claim 1, wherein the Wi-Fi module or router communicates the compliance notification signal.

3. The aerosol dispenser compliance device of claim 1, and wherein said press plate of said mechanical switch is in contact with the capacitive touch sensor in the closed switch state.

4. The aerosol dispenser compliance device of claim 1, wherein the mechanical switch further comprises a movable floating ring printed circuit board.

5. The aerosol dispenser compliance device of claim 1, wherein the electronics unit comprises a printed circuit board.

6. The aerosol dispenser compliance device as in claim 5 wherein said printed circuit board comprises an ESP09 microprocessor module, a super capacitor, and a resistor, wherein when said power supply is a battery and wherein a case where said battery does not supply necessary current at a fast enough speed, a draw from the circuit reduces a load from said battery, said super capacitor accumulates the current from said battery over a short period of time, and discharges the current at an increased speed to power said circuit board and said resistor controls the discharge of the current from said super capacitor.

7. The aerosol dispenser compliance device of claim 1, wherein the Wi-Fi module or router directs the notification signal to an Internet address or URL of a medical service provider or cloud storage system, where the user data of the Wi-Fi notification signal is stored and accessed by authorized users.

8. The aerosol dispenser compliance device of claim 7, wherein a failure to send a Wi-Fi notification signal to said medical service provider within a "failure to take" period results in an automatic communication to notify a $3^{rd}$ party that the user has failed to take a required dosage of aerosol mist.

9. The aerosol dispenser compliance device of claim 1, further comprising a key component for locking and unlocking said device for preventing spillage of medication and damage to said electronics;
    wherein separating a magnet and mouthpiece cap from a magnetically activated switch triggers a transition from an active state, to a dormant state, when said magnet and switch are proximate due to a presence of said mouthpiece cap prior to removal;
    wherein attaching said mouthpiece cap to the barrel of the housing triggers a transition from the dormant state to an active state;
    wherein a transition from the active state to the dormant state, by removing said mouthpiece cap from the housing generates an access signal;
    wherein a transition from the dormant state to the active state, by replacing said mouthpiece cap to a housing of said L-shaped elbowed hollow container generates a an aerosol mist dosage taken signal; and
    wherein if said aerosol mist dosage taken signal is generated within a predetermined period after said aerosol mist dosage access signal is generated, said microcontroller generates a compliance notification signal that is communicated to a Wi-Fi module or router within or attached to said electronics unit, to memorialize the apparent compliance.

10. The aerosol dispenser compliance device of claim 9, wherein the Wi-Fi module or router directs the notification signal to an Internet address or URL of a medical service provider or cloud storage system, where the user data of the Wi-Fi notification signal is stored and accessed by authorized users.

11. The aerosol dispenser compliance device of claim 10, wherein a failure to send a Wi-Fi notification signal to a medical service provider within a "failure to take" period results in an automatic communication to notify a $3^{rd}$ party that the user has failed to take a required aerosol mist dosage.

12. The aerosol dispenser compliance device of claim 10, wherein said electronics unit is located in an exterior attachment housing adjacent to the aerosol mist storage compartment.

13. The aerosol dispenser compliance device of claim 10, wherein said magnetically activated switch is a reed switch.

14. The aerosol dispenser compliance device of claim 13, wherein the reed switch includes a push button that overrides the signals generated by switching form a dormant to an active state or from an active to a dormant state.

15. The aerosol dispenser compliance device of claim 10, wherein said mouthpiece cap is slidably removable and replaceable.

16. The aerosol dispenser compliance device of claim 10, wherein said mouthpiece cap is removed from the housing.

17. A microcontroller-controlled method of providing aerosol compliance by use of an aerosol use compliance device for maintaining a patient's aerosol supply and monitoring a patient's access to an aerosol mist contained in the device to memorialize a patient's compliance with his/her aerosol-taking regimen, the aerosol compliance device comprising an electronics unit with electronic components including a microcontroller and memory, a housing with an inner storage compartment for storing aerosol, and a removable mouthpiece cap covering the inner storage compartment of said housing, said removable mouthpiece cap including at least one of:

a) a magnet, a magnetically activated switch with a magnet, or, b) a mechanical switch including a capacitive touch sensor element and a switch press element and wherein the press plate is in contact with the capacitive touch sensor in the closed switch state, wherein each said switch is used to detect removal of said mouthpiece cap and magnet away from said housing, and is responsive to a replacement of said mouthpiece cap and magnet to said housing, wherein separating the magnet and mouthpiece cap from the magnetically activated switch triggers a transition from an active state, to a dormant state;

wherein, when the switch is activated, the magnet and switch are proximate due to a presence of said mouthpiece cap prior to removal; and wherein attaching the mouthpiece cap to the housing triggers a transition from the dormant state to an active state, the method including steps of:

first generating an access signal upon removal of the removable mouthpiece cap from the housing and inner pill storage compartment, the access signal indicative of a transition from the active state to the dormant state;

second generating an aerosol dosage-taken signal when, within a predetermined amount of time, the removable mouthpiece cap is replaced on the housing and inner storage compartment, the aerosol dosage-taken compliance signal indicative of said patient's having inhaled the aerosol mist; and in response to an aerosol-taken signal, said microcontroller generating a compliance notification signal and provides said compliance notification signal to a Wi-Fi module or router within, attached to or coupled to the electronic unit to memorialize the apparent compliance.

* * * * *

UNITED STATES PATENT AND TRADEMARK OFFICE
CERTIFICATE OF CORRECTION

| | |
|---|---|
| PATENT NO. | : 11,224,556 B2 |
| APPLICATION NO. | : 17/016111 |
| DATED | : January 18, 2022 |
| INVENTOR(S) | : Shukla |

It is certified that error appears in the above-identified patent and that said Letters Patent is hereby corrected as shown below:

In the Claims

Column 21, In Claim 1, Lines 50-58 should read:
 an L-shaped, elbowed, hollow container, including an inner aerosol barrel storage compartment and a removable mouthpiece cap with a magnet for covering the L-shaped, elbowed, hollow container and the inner aerosol mist storage compartment; and
a wraparound attachment;
 wherein said wraparound attachment includes a power supply, a mechanical switch and an electronics unit including a microcontroller and a memory;

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*